(12) United States Patent
Li et al.

(10) Patent No.: US 11,486,633 B2
(45) Date of Patent: Nov. 1, 2022

(54) SMART REFRIGERATOR BASED ON BIG DATA ANALYSIS OF SERVER, HEALTH MANAGEMENT METHOD, AND SYSTEM

(71) Applicant: Shanghai Green Motive Technology Limited, Shanghai (CN)

(72) Inventors: Bo Li, Shanghai (CN); Laizhi Wang, Shanghai (CN)

(73) Assignee: Shanghai Green Motive Technology Limited, Shanghai (CN)

( * ) Notice: Subject to any disclaimer, the term of this patent is extended or adjusted under 35 U.S.C. 154(b) by 240 days.

(21) Appl. No.: 16/073,748

(22) PCT Filed: Dec. 29, 2017

(86) PCT No.: PCT/CN2017/119806
§ 371 (c)(1),
(2) Date: Jul. 27, 2018

(87) PCT Pub. No.: WO2019/095518
PCT Pub. Date: May 23, 2019

(65) Prior Publication Data
US 2021/0207883 A1    Jul. 8, 2021

(30) Foreign Application Priority Data

Nov. 20, 2017   (CN) .......................... 201721557450.6
Nov. 22, 2017   (CN) .......................... 201711173094.2

(51) Int. Cl.
*F25D 29/00* (2006.01)
*G16H 20/60* (2018.01)

(52) U.S. Cl.
CPC ......... *F25D 29/003* (2013.01); *F25D 29/008* (2013.01); *G16H 20/60* (2018.01);
(Continued)

(58) Field of Classification Search
None
See application file for complete search history.

(56) References Cited

U.S. PATENT DOCUMENTS

2015/0260449 A1 *   9/2015   Furuta .................... F25D 29/00
                                                              62/125
2016/0292409 A1 *   10/2016  Park ...................... A61B 5/7475
(Continued)

FOREIGN PATENT DOCUMENTS

CN       102937366 A       2/2013
CN       103884152 A       6/2014
(Continued)

OTHER PUBLICATIONS

International Search Report for International Application No. PCT/CN2017/119806, dated Jul. 30, 2018, 3 pages.

*Primary Examiner* — Paul B Yanchus, III
(74) *Attorney, Agent, or Firm* — USCH Law, PC

(57) ABSTRACT

Embodiments of this disclosure relate to electronic information, and disclose a smart refrigerator based on big data analysis of a server, including a refrigerator body, a collector, and a communication circuit. The collector is disposed in the refrigerator body and is used to collect human body health parameter information. The communication circuit is disposed in the refrigerator body and is connected to the collector, and is used to: upload human body health parameter information to a server, obtain a diet solution that is returned by the server after the server performs big data analysis on the human body health parameter information, and push the diet solution. This disclosure further discloses a health management method based on a smart refrigerator and a health management system. The smart refrigerator based on big data analysis of a server, the health management method based on a smart refrigerator, and the health (Continued)

management system that are provided in the embodiments of this disclosure can help a user properly plan healthy diets.

16 Claims, 8 Drawing Sheets

(52) U.S. Cl.
CPC ...... *F25D 2400/36* (2013.01); *F25D 2700/04* (2013.01); *Y10S 700/00* (2013.01)

(56) References Cited

U.S. PATENT DOCUMENTS

2017/0293966 A1* 10/2017 Huang ............... G06Q 30/0641
2017/0308666 A1* 10/2017 Thomson ............... G16H 10/60

FOREIGN PATENT DOCUMENTS

| | | |
|---|---|---|
| CN | 106161591 A | 11/2016 |
| CN | 106440610 A | 2/2017 |
| KR | 20140059978 A | 5/2014 |

* cited by examiner

SMART REFRIGERATOR BASED ON BIG DATA ANALYSIS OF SERVER, HEALTH MANAGEMENT METHOD, AND SYSTEM

CROSS-REFERENCE TO RELATED APPLICATIONS

The present disclosure is a National Stage Application of PCT/CN2017/119806, filed Dec. 29, 2017, which claims the benefit of and priority to Chinese Patent Application No. 201721557450.6, entitled "SMART REFRIGERATOR BASED ON BIG DATA ANALYSIS OF SERVER" and filed on Nov. 20, 2017, and Chinese Patent Application No. 201711173094.2, entitled "SMART REFRIGERATOR BASED ON BIG DATA ANALYSIS OF SERVER, HEALTH MANAGEMENT METHOD, AND SYSTEM" and filed on Nov. 22, 2017, all of which are incorporated herein by reference in their entireties.

TECHNICAL FIELD

Embodiments of this application relate to electronic information, in particular to a smart refrigerator based on big data analysis of a server, a health management method based on a smart refrigerator, and a health management system.

BACKGROUND

With the development of social life, living standards of people gradually improve, and more varieties and quantities of food ingredients are comestible. People gradually tend to store various foods such as vegetables and fruits by using refrigerators, to conveniently take the foods at any time.

It is found by the inventor that, because users have different diets, poor diet habits may be formed and affect their health. For health problems caused by the poor diet habits of the users, how to help people make a proper plan to implement healthy diets is crucial.

SUMMARY

An objective of some embodiments of this disclosure is to provide a smart refrigerator based on big data analysis of a server, a health management method based on a smart refrigerator, and a health management system, to help a user properly plan healthy diets.

To resolve the foregoing problem, an embodiment of this disclosure provides a smart refrigerator based on big data analysis of a server, including a refrigerator body, a collector, and a communication circuit, wherein the collector is disposed in the refrigerator body and is used to collect human body health parameter information; and the communication circuit is disposed in the refrigerator body and is connected to the collector, and the communication circuit is used to: upload the human body health parameter information to a server, obtain a diet solution that is returned by the server after the server performs big data analysis on the human body health parameter information, and push the diet solution.

An embodiment of this disclosure further provides a health management method based on a smart refrigerator, including the following steps:

collecting human body health parameter information;

uploading the human body health parameter information;

obtaining a diet solution that is returned after big data analysis is performed on the human body health parameter information; and pushing the diet solution.

An embodiment of this disclosure further provides a health management system, including a smart refrigerator and a server, where the smart refrigerator is used to collect human body health parameter information, and upload the human body health parameter information to the server; and the server is used to perform big data analysis on human body health parameter information, to obtain a diet solution for a user to view.

Compared with existing technologies, according to the embodiments of this disclosure, the collector disposed in the refrigerator body collects the human body health parameter information, and the communication circuit uploads the human body health parameter information to the server. The server returns the diet solution after performing big data analysis, and the communication circuit pushes the diet solution. In this way, after the server performs big data analysis on the human body health parameter information collected by the collector, a potential health problem of a human body can be found, and a proper diet solution for resolving the health problem of the human body can be obtained, so that a user can properly plan healthy diets according to the diet solution.

In addition, the communication circuit is further used to upload information about food ingredients stored in the refrigerator body to the server, and food ingredients in the diet solution are the food ingredients stored in the refrigerator body. The user can directly select food ingredients from the refrigerator, and properly prepare the food ingredients according to the diet solution conveniently and quickly.

In addition, the collector includes a conductive electrode and a conversion circuit;

the conductive electrode is used to come into contact with skin of a human body and form an alternating current conductive loop with the human body, to receive an electrical signal of the human body; and the conversion circuit is connected to the conductive electrode, and the conversion circuit is used to convert the electrical signal of the human body into the human body health parameter information.

In addition, the smart refrigerator further includes a display screen, the display screen is disposed on the refrigerator body and is connected to the communication circuit, and the display screen is used to receive and display the diet solution pushed by the communication circuit. The display screen helps the user directly view the diet solution on the refrigerator, and arrange diets according to the food ingredients stored in the refrigerator or supplement food ingredients in the refrigerator.

In addition, the communication circuit is further used to obtain and push an exercise solution that is returned by the server after the server performs big data analysis on the human body health parameter information; and the display screen is further used to receive and display the exercise solution pushed by the communication circuit.

In addition, while the human body health parameter information is uploaded, information about the food ingredients stored in the smart refrigerator is uploaded, and food ingredients in the diet solution are the food ingredients stored in the refrigerator body.

In addition, the smart refrigerator receives the diet solution, and pushes the diet solution to the user.

In addition, the health management system further includes a mobile terminal. The mobile terminal is used to receive the diet solution, and push the diet solution to the user. This helps the user directly view the diet solution on the mobile terminal in use, and learn, at any time, improvements needed in the diet solution of the user. In addition, the user may take the mobile terminal to purchase and supplement the food ingredients, so as to properly arrange the diets.

BRIEF DESCRIPTION OF THE DRAWINGS

One or more embodiments are described as examples with reference to the corresponding figures in the accompanying drawings, and the examples do not constitute a limitation to the embodiments. Elements with the same reference numerals in the accompanying drawings represent similar elements. The figures in the accompanying drawings do not constitute a proportion limitation unless otherwise stated.

DETAILED DESCRIPTION

To make objectives, technical solutions, and advantages of embodiments of this disclosure clearer, the following further describes the embodiments of this disclosure in detail with reference to the accompanying drawings. A person of ordinary skill in the art may understand that technical details are described in the embodiments of this disclosure to make readers more easily understand this disclosure. However, if the technical details and various changes and modifications based on the following embodiments are not described, the technical solutions to be protected in this disclosure can also be implemented.

Figure 1:
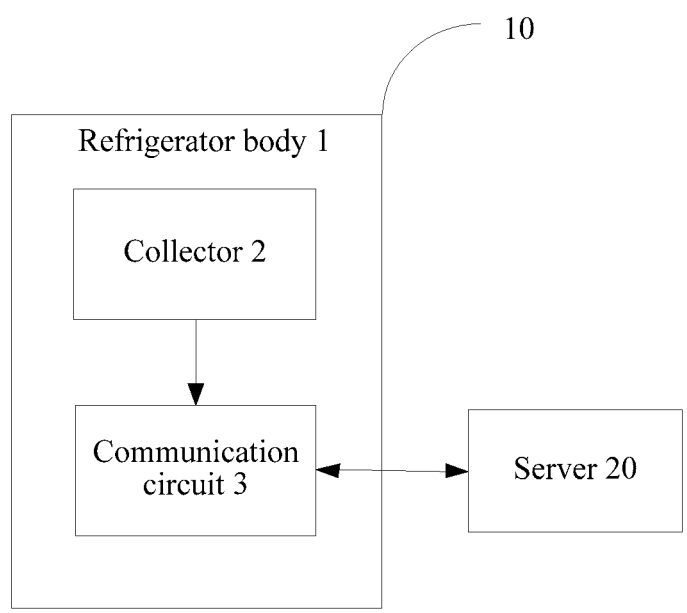
FIG. 1 is a schematic structural diagram of a smart refrigerator based on big data analysis of a server according to a first embodiment of this disclosure.
Figure 2:
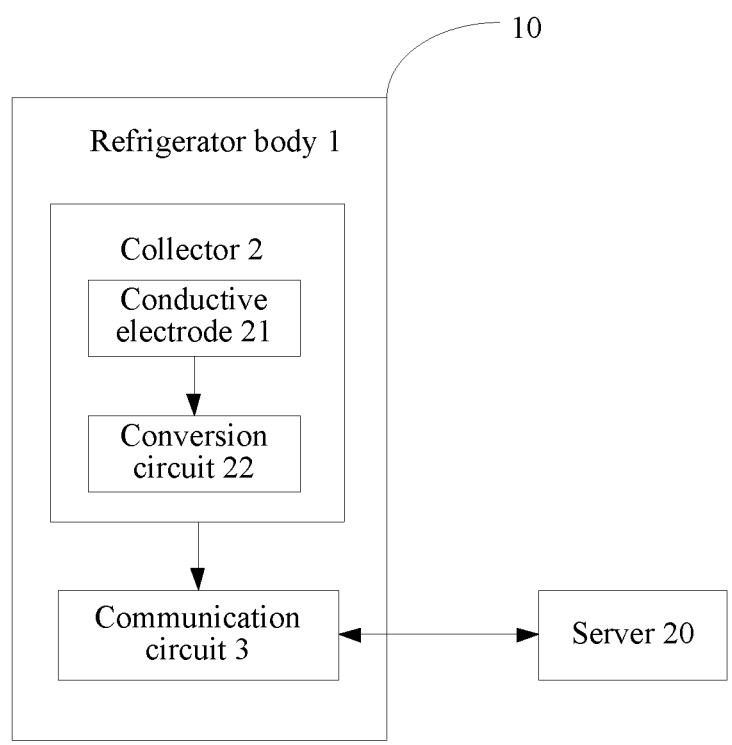
FIG. 2 is another schematic structural diagram of a smart refrigerator based on big data analysis of a server according to the first embodiment of this disclosure.

A first embodiment of this disclosure relates to a smart refrigerator 10 based on big data analysis of a server 20. As shown in FIG. 1, the smart refrigerator 10 includes a refrigerator body 1, a collector 2, and a communication circuit 3. The collector 2 is disposed in the refrigerator body 1 and is used to collect human body health parameter information. The communication circuit 3 is disposed in the refrigerator body 1 and is connected to the collector 2. The communication circuit 3 is used to: upload the human body health parameter information to the server 20, obtain a diet solution that is returned by the server 20 after the server 20 performs big data analysis on the human body health parameter information, and push the diet solution.

The smart refrigerator 10 may obtain the human body health parameter information by using a bioelectrical impedance analysis (BIA) method. The BIA method is a method for indirectly evaluating body composition. The basic idea is that, when a weak multi-frequency alternating current signal is imported into a human body, a current flows along body fluid with a small resistance and good conductivity. Electrical conductivity of a current path depends on water content, and may be represented by using a measurement value of impedance. Therefore, a statistical relationship exists between an electrical impedance characteristic of the human body and body composition, and the body composition may be measured based on a bioelectrical impedance technology.

Compared with existing technologies, according to this embodiment of this disclosure, the collector 2 disposed in the refrigerator body 1 collects the human body health parameter information, and the communication circuit 3 uploads the human body health parameter information to the server 20. The server returns the diet solution after performing big data analysis, and the communication circuit 3 pushes the diet solution. In this way, after the server 20 performs big data analysis on the human body health parameter information collected by the collector 2, a potential health problem of a human body can be found, and a proper diet solution for resolving the health problem of the human body can be obtained, so that a user can properly plan healthy diets directly according to the provided diet solution.

A method for collecting the human body health parameter information by the collector 2 may include: conducting an effective micro current after the collector 2 comes into contact with the human body (for example, both hands), and generating the human body health parameter information such as a body metabolic rate, fat, visceral fat, bone mass, muscle, protein, water content, or a body mass index (BMI) by calculating parameters of electrical impedance of the human body.

In this embodiment, the user may select food ingredients according to the diet solution. If the food ingredients in the diet solution are already stored in the refrigerator, the user may directly select the food ingredients and arrange diets. If the food ingredients in the diet solution are not stored in the refrigerator, the user may supplement the food ingredients and then arrange the diets.

The following specifically describes implementation details of the smart refrigerator based on big data analysis of the server in this embodiment. The following describes only implementation details provided for facilitating understanding, and is not necessary for implementing this solution.

Figure 10:
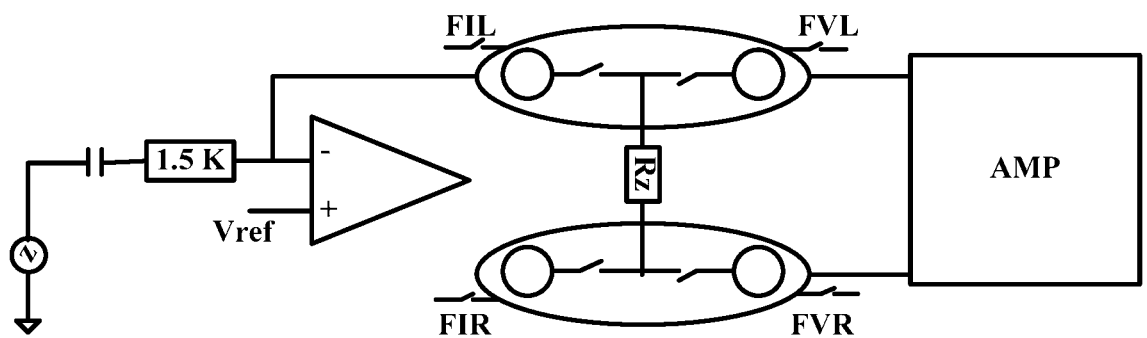
FIG. 10 is a schematic diagram of a conversion circuit of the smart refrigerator according to the first embodiment of this disclosure.

In this embodiment, as shown in FIG. 2 and FIG. 7 to FIG. 9, the collector 2 specifically includes conductive electrodes 21 and a conversion circuit 22. The conductive electrodes 21 are used to come into contact with skin of the human body and form an alternating current conductive loop with the human body, to receive an electrical signal of the human body. The conversion circuit 22 is connected to the conductive electrodes 21, and the conversion circuit 22 is used to convert the electrical signal of the human body into the human body health parameter information. For example, FIG. 10 is a schematic diagram of a conversion circuit. Specifically, the conductive electrodes 21 may be conductive strips 210. The conductive strips 210 are disposed on a housing of the refrigerator body 1. The number of the conductive strips 210 may be 2, 4, or more, which is not enumerated herein. When the skin of the human body comes into contact with the conductive strips 210, the skin of the human body and the conductive strips 210 form an alternating current conductive loop, and the conductive strips 210 may receive the electrical signal of the human body. The conductive strips 210 are connected to the conversion circuit 22, and the conductive strips transmit the electrical signal to the conversion circuit 22. The conversion circuit 22 converts the electrical signal of the human body into human body health parameter information such as a body metabolic rate, fat, visceral fat, bone mass, muscle, protein, water content, and a BMI.

Figure 3:
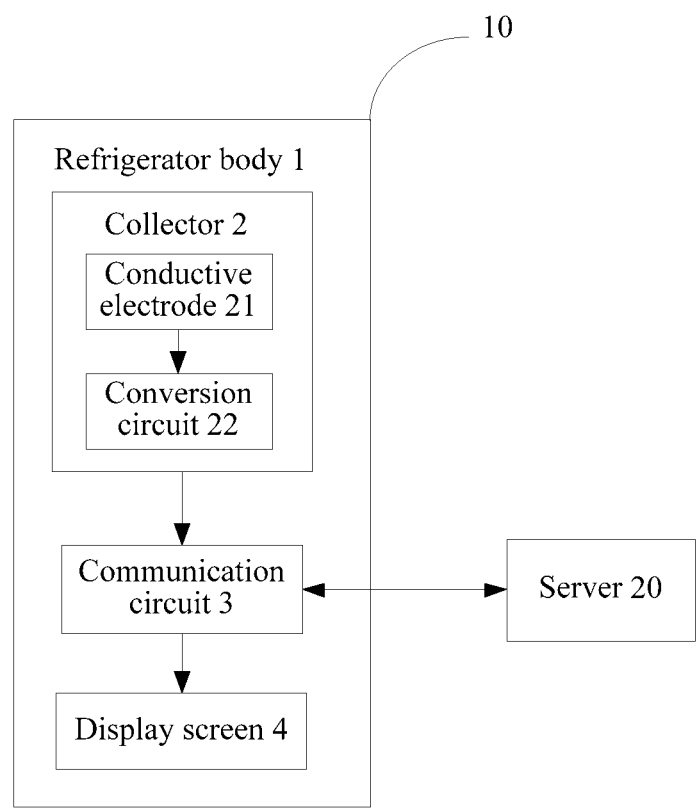
FIG. 3 is still another schematic structural diagram of a smart refrigerator based on big data analysis of a server according to the first embodiment of this disclosure.

Specifically, as shown in FIG. 3, the smart refrigerator 10 further includes a display screen 4. The display screen 4 is disposed on the refrigerator body 1 and is connected to the communication circuit 3, and the display screen 4 is used to receive and display the diet solution pushed by the communication circuit 3. The display screen 4 helps the user directly view the diet solution on the refrigerator, and arrange diets according to the food ingredients stored in the refrigerator or arrange diets after supplementing the food ingredients in the refrigerator.

It should be noted that, the communication circuit 3 is further used to obtain and push an exercise solution that is returned by the server 20 after the server 20 performs big data analysis on the human body health parameter information, and the display screen 4 is further used to receive and display the exercise solution pushed by the communication circuit 3. Because the server 20 makes an exercise plan for the user to do exercise according to a human body health status after performing the big data analysis on the human body health parameter information, in addition to having proper diets, the user can improve the health status by doing exercise.

Preferably, the communication circuit 3 is further used to upload information about food ingredients stored in the refrigerator body 1 to the server, and food ingredients in the diet solution are the food ingredients stored in the refrigerator body 1. The user can directly select the food ingredients from the refrigerator, and prepare the food ingredients according to the diet solution conveniently and quickly.

Figure 4:
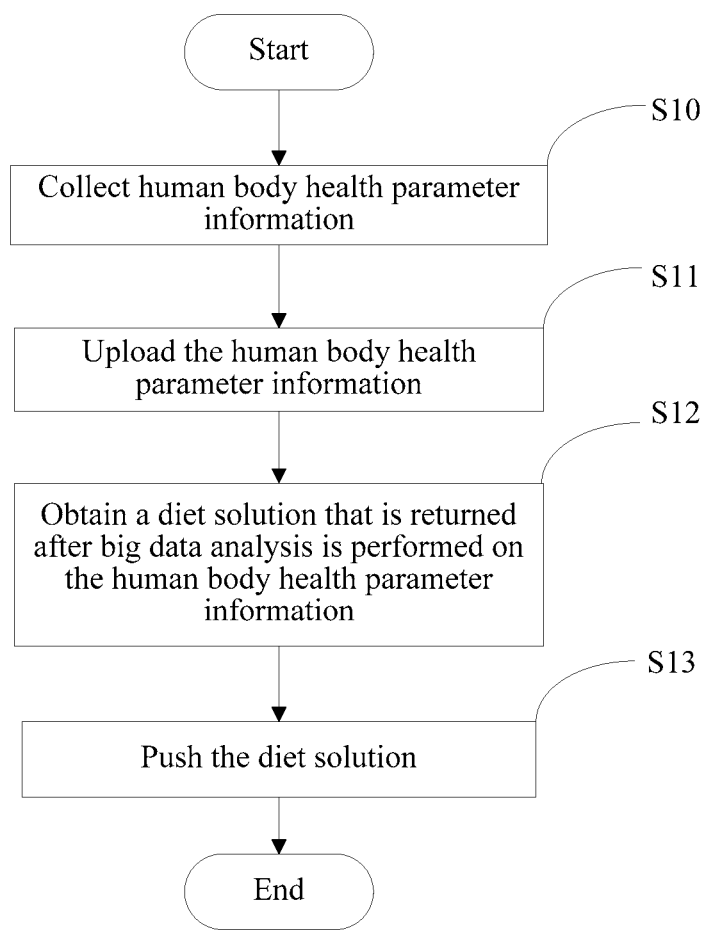
FIG. 4 is a flowchart of a health management method based on a smart refrigerator according to a second embodiment of this disclosure.

A second embodiment of this disclosure relates to a health management method based on a smart refrigerator. As shown in FIG. 4, the following steps are included.

Step S10: Collect human body health parameter information.

Specifically, a conductive electrode of the smart refrigerator first comes into contact with skin of a human body and forms an alternating current conductive loop, to receive an electrical signal of the human body. Then a conversion circuit converts the electrical signal of the human body into the human body health parameter information.

Step S11: Upload the human body health parameter information.

Specifically, a communication circuit of the smart refrigerator uploads the human body health parameter information to a server, and the server obtains a diet solution after performing big data processing on the human body health parameter information. More specifically, the server obtains human body health status information in a process of analyzing the human body health parameter information, and recommends a proper diet solution according to the human body health status information.

Preferably, while the human body health parameter information is uploaded, information about food ingredients stored in the smart refrigerator is uploaded, and food ingredients in the diet solution are the food ingredients stored in the refrigerator body. A user can directly select the food ingredients from the refrigerator, and prepare the food ingredients according to the diet solution conveniently and quickly.

Step S12: Obtain a diet solution that is returned after big data analysis is performed on the human body health parameter information.

Specifically, the communication circuit obtains the returned diet solution. The diet solution may include food ingredient names, recipes, or the like.

Step S13: Push the diet solution.

Specifically, the communication circuit of the smart refrigerator pushes the diet solution to the user. The user may select the food ingredients from the refrigerator or purchase the food ingredients, and cook foods according to the recipes in the diet solution, to properly arrange diets.

Figure 5:
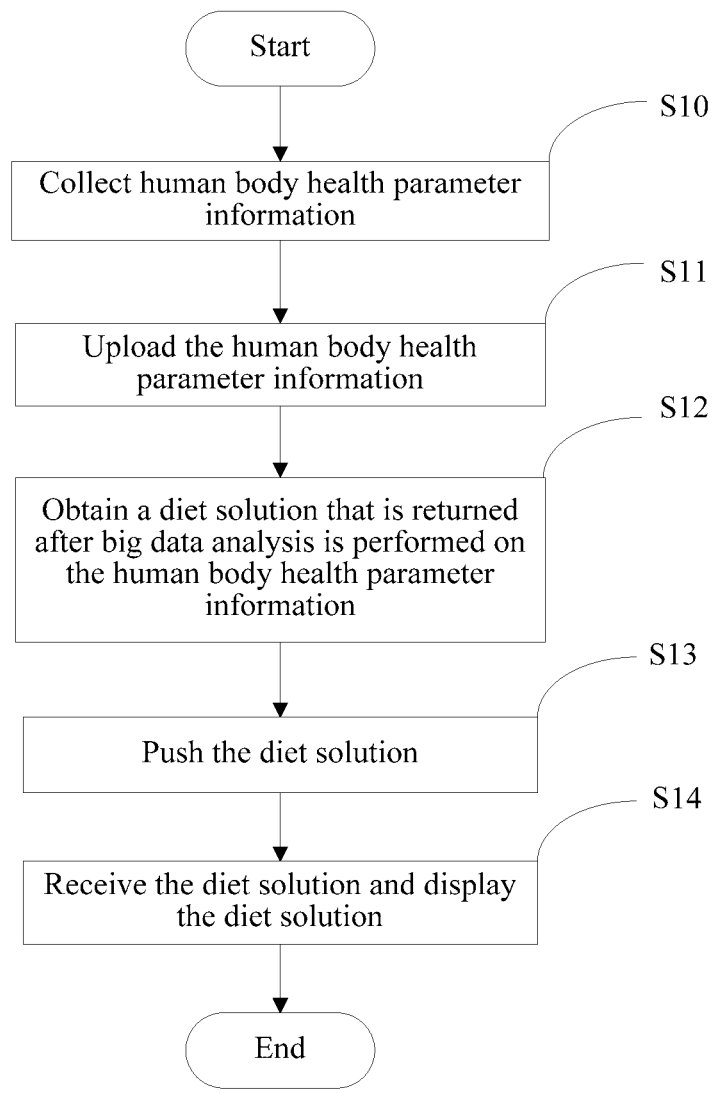
FIG. 5 is another flowchart of a health management method based on a smart refrigerator according to the second embodiment of this disclosure.

In this embodiment, as shown in FIG. 5, after step S13, the health management method further includes step S14 of receiving the diet solution and displaying the diet solution.

Specifically, a display screen of the smart refrigerator receives the diet solution and displays the diet solution. The user may view the diet solution conveniently and quickly by using the display screen, to select the food ingredients from the refrigerator or purchase the food ingredients for cooking.

The foregoing methods are divided into steps for clear description. When the methods are achieved, the steps may be combined into one step or some steps may be divided into more steps, which shall fall within the protection scope of the present disclosure provided that the steps include a same logic relation; the algorithm and flow to which inessential modification is made or inessential design is introduced without changing the core design of the algorithm and flow shall fall within the protection scope of the present disclosure.

Figure 6:
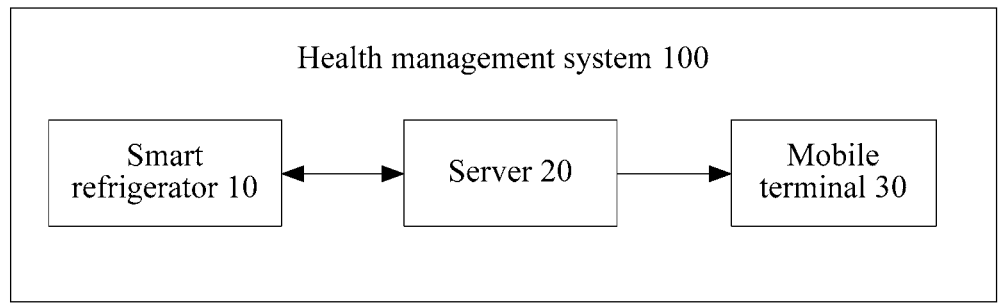
FIG. 6 is a schematic structural diagram of a health management system according to a third embodiment of this disclosure.
Figure 7:
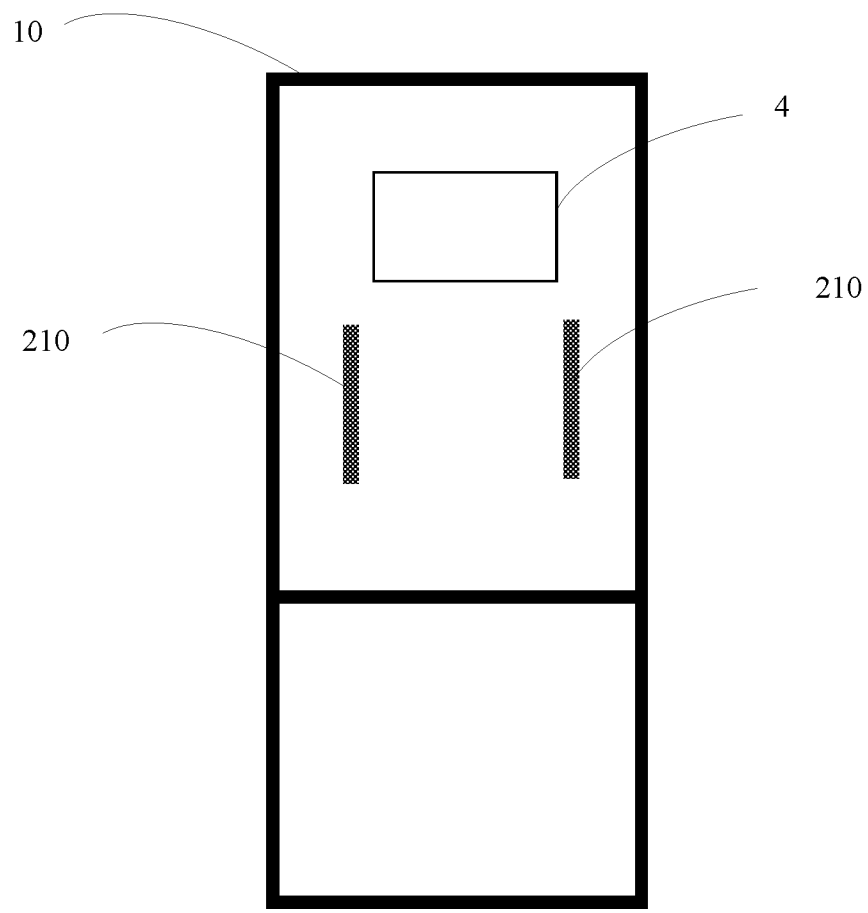
FIG. 7 is a schematic structural outside view of a smart refrigerator according to the first embodiment of this disclosure.
Figure 8:
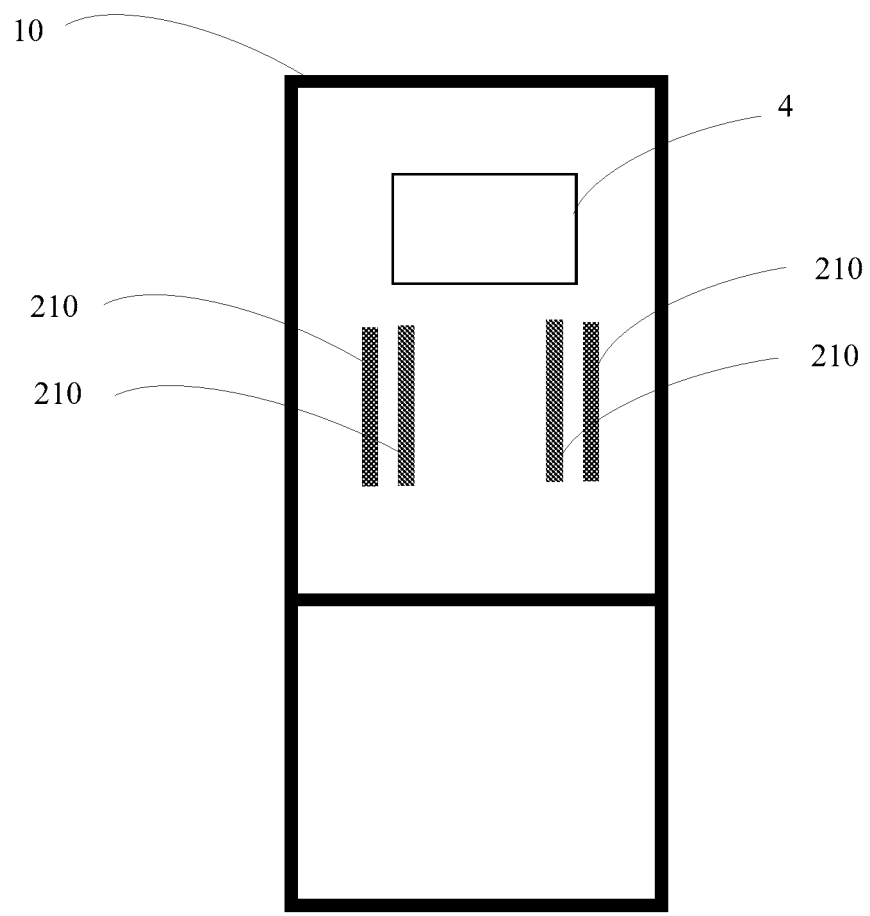
FIG. 8 is another schematic structural outside view of the smart refrigerator according to the first embodiment of this disclosure.
Figure 9:
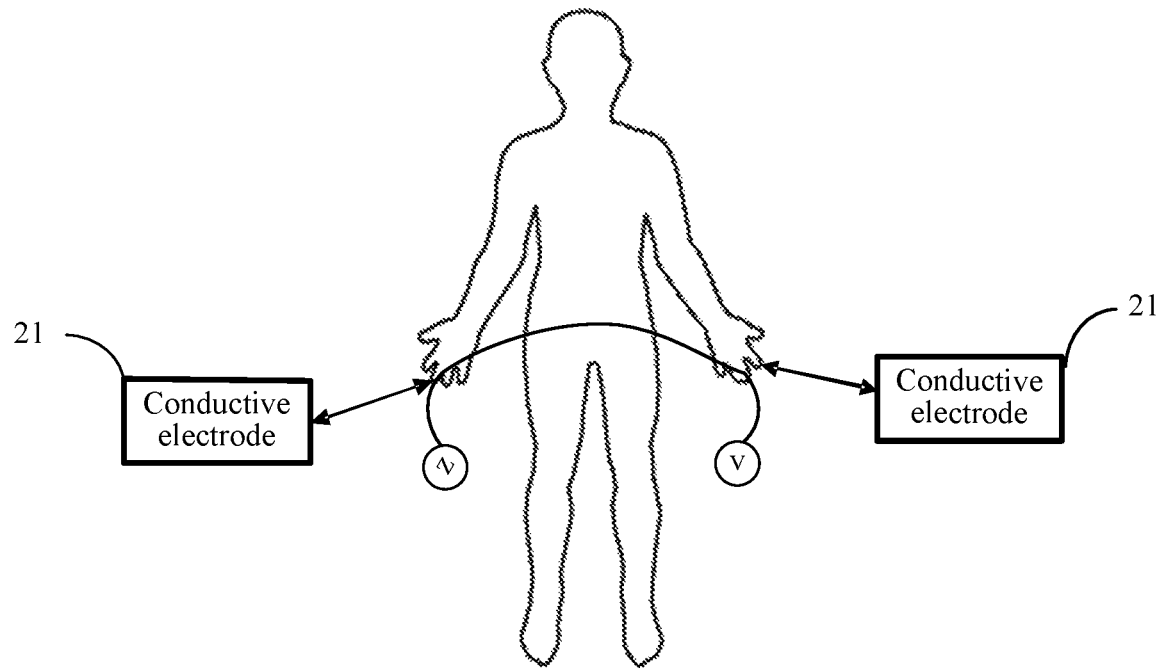
FIG. 9 is a schematic diagram of an alternating current conductive loop that is formed after skin of a human body comes into contact with a conductive electrode.

A third embodiment of this disclosure relates to a health management system 100. As shown in FIG. 6, the health management system 100 includes: a smart refrigerator 10 and a server 20. The smart refrigerator 10 collects human body health parameter information, and uploads the human body health parameter information to the server 20. The server 20 performs big data analysis on the human body health parameter information to obtain a diet solution for a user to view.

Specifically, after the server performs big data analysis on the human body health parameter information to obtain the diet solution, the smart refrigerator 10 receives the diet solution, and pushes the diet solution to the user for viewing.

In addition, the health management system 100 further includes a mobile terminal 30. While the smart refrigerator 10 receives the diet solution and pushes the diet solution to the user, the mobile terminal 30 receives the diet solution and pushes the diet solution to the user for viewing. In this way, the user can directly view the diet solution on the mobile terminal in use, and learn, at any time, improvements needed to make to diets of the user conveniently. In addition, the user may take the mobile terminal to supplement food ingredients, so as to properly arrange the diets.

A person of ordinary skill in the art may understand that the foregoing embodiments are specific examples of this disclosure, but in practical application, various changes may be made in the form and details without departing from the spirit and scope of this disclosure.

What is claimed is:

1. A smart refrigerator based on big data analysis at a server, comprising a refrigerator body, a collector, and a communication circuit, wherein the collector is disposed in the refrigerator body and is configured to collect human body health parameter information; and the communication circuit is disposed in the refrigerator body and is connected to the collector, and the communication circuit is configured to: upload the human body health parameter information to the server, obtain a diet solution that is returned by the server after the server performs big data analysis on the human body health parameter information, and push the diet solution;

wherein the collector comprises conductive electrodes and a conversion circuit, the conductive electrodes are configured to come into contact with skin of a human body, to form an alternating current conductive loop with the human body, and to receive an electrical signal of the human body, the conversion circuit is connected to the conductive electrodes, and the conversion circuit is configured to convert the electrical signal of the human body into the human body health parameter information.

2. The smart refrigerator based on big data analysis at of a server according to claim 1, wherein the communication circuit is further configured to upload information about food ingredients stored in the refrigerator body to the server, and food ingredients in the diet solution are the food ingredients stored in the refrigerator body.

3. The smart refrigerator based on big data analysis at a server according to claim 1, wherein the smart refrigerator further comprises a display screen, the display screen is disposed on the refrigerator body and is connected to the communication circuit, and the display screen is configured to receive and display the diet solution pushed by the communication circuit.

4. The smart refrigerator based on big data analysis at a server according to claim 3, wherein the communication circuit is further configured to obtain and push an exercise solution that is returned by the server after the server performs big data analysis on the human body health parameter information; and the display screen is further configured to receive and display the exercise solution pushed by the communication circuit.

5. A health management method based on a smart refrigerator, comprising: collecting human body health parameter information; uploading the human body health parameter information; obtaining a diet solution that is returned after big data analysis is performed on the human body health parameter information; and pushing the diet solution;

wherein the smart refrigerator comprises conductive electrodes and a conversion circuit, and collecting the human body health parameter information comprises: forming, by the conductive electrodes after coming into contact with skin of a human body, an alternating current conductive loop, to receive an electrical signal of the human body; and converting, by the conversion circuit, the electrical signal of the human body into the human body health parameter information.

6. The health management method based on a smart refrigerator according to claim 5, wherein while the human body health parameter information is uploaded, information about food ingredients stored in the smart refrigerator is uploaded, and food ingredients in the diet solution are the food ingredients stored in the refrigerator body.

7. A health management system, comprising a smart refrigerator and a server, wherein the smart refrigerator is configured to collect human body health parameter information, and upload the human body health parameter information to the server; and the server is used configured to perform big data analysis on the human body health parameter information, to obtain a diet solution for a user to view;

wherein the smart refrigerator comprises conductive electrodes and a conversion circuit, the conductive electrodes are configured to come into contact with skin of a human body, to form an alternating current conductive loop with the human body, and to receive an electrical signal of the human body, the conversion circuit is connected to the conductive electrodes, and the conversion circuit is configured to convert the electrical signal of the human body into the human body health parameter information.

8. The health management system according to claim 7, wherein the smart refrigerator is configured to receive the diet solution, and push the diet solution to the user.

9. The health management system according to claim 7, further comprising a mobile terminal, wherein the mobile terminal is configured to receive the diet solution, and push the diet solution to the user.

10. The smart refrigerator based on big data analysis at a server according to claim 1, wherein the human body health parameter information comprises a body metabolic rate, fat, visceral fat, bone mass, muscle, protein, water content, and/or a body mass index.

11. The smart refrigerator based on big data analysis at a server according to claim 3, wherein the conductive electrodes are conductive strips, and the conductive strips are disposed on a housing of the refrigerator body.

12. The smart refrigerator based on big data analysis at a server according to claim 11, wherein there are two or four conductive strips.

13. The health management method based on a smart refrigerator according to claim 6, wherein uploading the human body health parameter information comprises: uploading, by a communication circuit, the human body health parameter information to a server, and obtaining, by the server after performing big data processing on the human body health parameter information, a diet solution.

14. The health management method based on a smart refrigerator according to claim 6, wherein obtaining a diet solution that is returned after big data analysis is performed on the human body health parameter information comprises: obtaining, by the server, human body health status information in a process of analyzing the human body health parameter information, and recommending a proper diet solution according to the human body health status information.

15. The health management method based on a smart refrigerator according to claim 6, wherein the diet solution comprises food ingredient names and/or recipes.

16. The health management method based on a smart refrigerator according to claim 6, wherein after the step of pushing the diet solution, the method further comprises: receiving the diet solution and displaying the diet solution.

* * * * *